(12) United States Patent
Marshall et al.

(10) Patent No.: US 8,831,748 B2
(45) Date of Patent: *Sep. 9, 2014

(54) MEDICAL ELECTRICAL ELECTRODES WITH CONDUCTIVE POLYMER

(75) Inventors: Mark T. Marshall, Forest Lake, MN (US); Teresa A. Whitman, Dayton, MN (US); Suping Lyu, Maple Grove, MN (US); Elizabeth K. Nagy, Maple Grove, MN (US); David S. Olson, Scandia, MN (US)

(73) Assignee: Medtronic, Inc., Minneapolis, MN (US)

( * ) Notice: Subject to any disclaimer, the term of this patent is extended or adjusted under 35 U.S.C. 154(b) by 749 days.

This patent is subject to a terminal disclaimer.

(21) Appl. No.: 12/414,265

(22) Filed: Mar. 30, 2009

(65) Prior Publication Data

US 2009/0187236 A1 Jul. 23, 2009

Related U.S. Application Data

(63) Continuation of application No. 11/113,867, filed on Apr. 25, 2005, now Pat. No. 7,512,447.

(51) Int. Cl.
*A61N 1/05* (2006.01)

(52) U.S. Cl.
CPC .................................. *A61N 1/0563* (2013.01)
USPC .......................................................... 607/122

(58) Field of Classification Search
USPC .......................................................... 607/122
See application file for complete search history.

(56) References Cited

U.S. PATENT DOCUMENTS

| | | | | |
|---|---|---|---|---|
| 3,815,611 A | * | 6/1974 | Denniston, III | 607/8 |
| 4,934,049 A | * | 6/1990 | Kiekhafer et al. | 29/883 |
| 5,115,818 A | * | 5/1992 | Holleman et al. | 607/122 |
| 5,580,699 A | * | 12/1996 | Layman et al. | 430/311 |
| 5,676,784 A | * | 10/1997 | McGaffigan | 156/172 |
| 5,791,036 A | * | 8/1998 | Goodin et al. | 29/423 |
| 2003/0139794 A1 | * | 7/2003 | Jenney et al. | 607/122 |
| 2005/0203604 A1 | * | 9/2005 | Brabec et al. | 607/122 |

* cited by examiner

*Primary Examiner* — Eric D. Bertram
(74) *Attorney, Agent, or Firm* — Carol F. Barry

(57) ABSTRACT

A medical electrical electrode includes an elongated conductive coil located over a lead body, and a conductive polymer material in contact with the lead body and located between individual coils of the elongated conductive coil. In certain embodiments, the conductive polymer is a polymer (e.g., silicone) implanted with a conductive filler (e.g., carbon black). In certain embodiments, the conductive polymer material is generally isodiametric with an outer diameter of the individual coils of the elongated conductive coil. A medical electrical electrode is fabricated by sliding an elongated conductive coil over a length of a lead body, dispersing a conductive polymer on the helical coil, inserting a tubing over the elongated conductive coil, distributing the polymer material between individual turns of the elongated conductive coil, heating the tubing so the tubing shrinks around the elongated conductive coil, and removing the tubing.

7 Claims, 9 Drawing Sheets

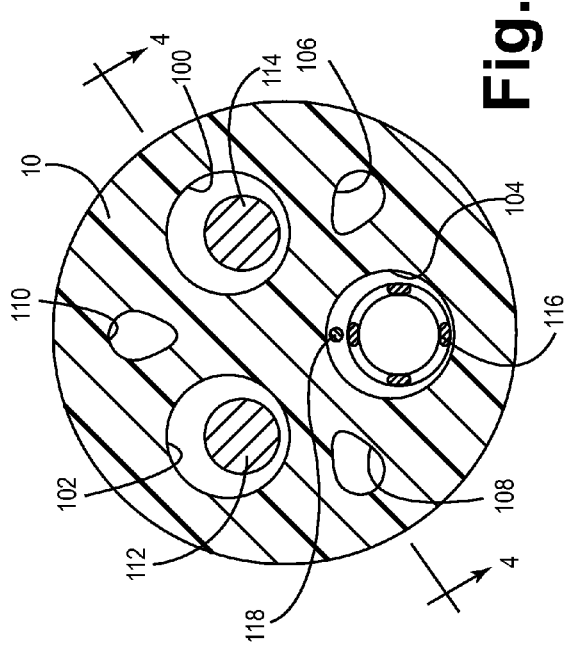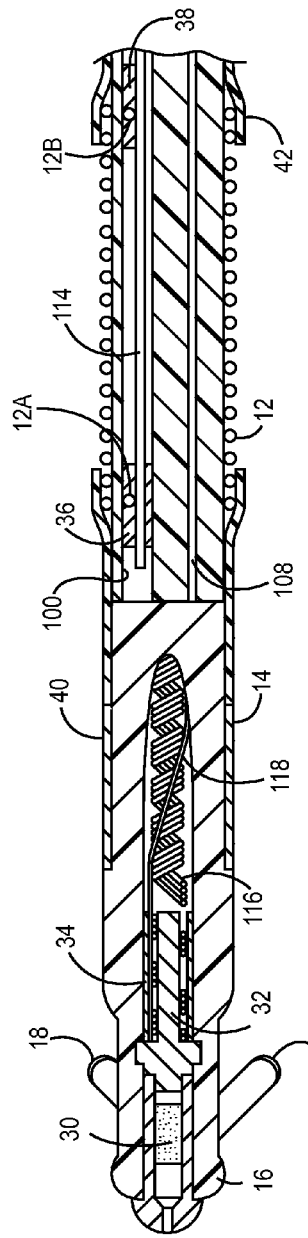

MEDICAL ELECTRICAL ELECTRODES WITH CONDUCTIVE POLYMER

CROSS-REFERENCE TO RELATED APPLICATION

This application is a continuation of U.S. patent application Ser. No. 11/113,867 filed on Apr. 25, 2005, now U.S. Pat. No. 7,512,447. The disclosure(s) of the above application(s) is (are) incorporated herein by reference.

FIELD

The present invention relates to medical electrical stimulation electrodes generally, and more specifically, to defibrillation electrodes.

BACKGROUND SECTION

Implantable medical devices are used to provide therapy to patients suffering from a variety of conditions. Examples of implantable medical devices are pacemakers and cardioverter-defibrillators (ICDs), which are electronic medical devices that monitor the electrical activity of the heart and provide electrical stimulation to one or more of the heart chambers, when necessary. For example, pacemakers are designed to sense arrhythmias, i.e., disturbances in heart rhythm, and in turn, provide appropriate electrical stimulation pulses, at a controlled rate, to selected chambers of the heart in order to correct the arrhythmias and restore the proper heart rhythm. The types of arrhythmias that may be detected and corrected by pacemakers include bradycardias, which are unusually slow heart rates, and certain tachycardias, which are unusually fast heart rates.

Cardioverter-defibrillators (ICDs) also detect arrhythmias and provide appropriate electrical stimulation pulses to selected chambers of the heart to correct the abnormal heart rate. In contrast to pacemakers, however, an ICD can also provide pulses that are much stronger and less frequent. This is because ICDs are generally designed to correct fibrillation, which is a rapid, unsynchronized quivering of one or more heart chambers, and severe tachycardias, where the heartbeats are very fast but coordinated. To correct such arrhythmias, ICDs deliver low, moderate, or high-energy shocks to the heart.

The electrical energy for the shocks generated by ICDs is delivered to the heart via electrical stimulation electrodes. One or more capacitors within the ICD are capable of rapidly delivering that energy to the patient's heart through leads that electrically connect the capacitors to the electrodes. In order to provide timely therapy to the patient after the detection of ventricular fibrillation, for example, it is necessary to charge the capacitors with the required amount of energy as quickly as possible. Thus, a battery in an ICD generally has a high rate capability to provide the necessary current to charge the capacitors.

In some designs, ICDs use large surface area electrodes either to be placed endocardially, epicardially or subcutaneously. One well-known approach of providing a large surface area electrode is to employ an elongated exposed coil of biocompatible metal. As is known, such elongated coils can be used with a wide variety of leads. For example, with an epicardial lead, an elongated coil serving as the electrode can be mounted around the exterior of an insulative lead body. In this context, it has been desirable to stabilize the electrode coil with respect to the lead body, both to provide mechanical integrity and to prevent fibrous growth around the individual coils of the electrode coil. In some designs, this has been accomplished by sliding the electrode coil over the lead body and backfilling spaces between the coil and the lead body with a plastic material. The exterior surface of the electrode coil is then machined to provide a smooth surface. Alternatively, the backfilling material may be removed by means of well-known plasma etching methods. Generally, the process can be varied as desired in order to provide the warranted amount of exposed surface area for the coil wire. For example, the removal process may be provided so that the backfilling material only extends radially outward between the turns of the coil from about one-third to one-half the diameter of the coil wire.

Alternative methods of making similar defibrillation lead structures without the necessity of using a backfilling can employ materials such as polyurethane to stabilize the electrode coil and to fill between the turns of the coil. In certain methods, a plastic tube can be stretched so that it displays an inner and outer diameter less than the inner and outer diameter of the tube in a relaxed state. An electrode coil having a inner diameter less than the outer diameter of the tube in its relaxed state is then slide over the stretched tube, after which the tube is released, allowing it to return to its previous length. However, after such release, the tube remains in a partially compressed state because of its contact with the electrode coil throughout the coil's length. Thereafter, a mandrel having an outer diameter greater than the inner diameter of the tubing in its compressed state is passed into the tubing, to further compress the tubing between the mandrel and the conductor coil. The assembly is thereafter heated, allowing the tubing to flow into spaces between the electrode coil.

While the methods of providing a plastic or polyurethane material between the electrode coil and lead body described above have been generally used, each has shortcomings. One particular shortcoming, with respect to both methods, is that there is variability in the pressure applied to the plastic or polyurethane material when situated between the individual coils of the electrode coil. As such, an uneven structure is often produced in which the plastic or polyurethane material does not flow outward to a consistent dimension between the individual coils. The present invention is directed to overcoming, or at least reducing the effects of, this shortcoming as well as others.

BRIEF SUMMARY

Generally, coil type electrodes of defibrillators are not uniform in terms of their geometry and electric field, which may cause cell in-growth and uneven electric discharge. The ideal materials to coat such coil electrodes are those that (1) are reasonably electric conductive, (2) are flexible and strong and have good adhesion to other parts so that the electrodes can be made flexible and durable, (3) have solid structure so cell in-growth is prevented, and (4) are biostable and compatible for implant in humans. In certain embodiments, such material is a polymer filled with a conductive filler. Silicone is generally considered a qualified polymer for implant applications. Carbon black can be made to have good conductivity, good polymeric (flexible and strong) mechanical properties, and good adhesion properties to metal. As such, carbon black can be used as the conductive filler. Carbon black is also quite inert. Therefore, a carbon black filled silicone has been found to be compatible as well as biostable in this application. Also, carbon black filled silicone is solid, which makes it different from other porous conductive materials e.g. ETFE (Ethylene-Tetrafluoroethylene) porous tubing. As such, cell in-growth can be prevented.

The conductive polymer is used to backfill the defibrillation coils of a high voltage lead and because of its conductive nature, allows complete coverage of the area between the coils of the defibrillation electrode without affecting the electrical performance of the lead. The increase in backfill creates a smoother outer surface that can help prevent tissue ingrowth and may improve lead extraction. The process of applying the conductive backfill to the defibrillation electrode is automated and shrink tubing is used to form the polymer.

BRIEF DESCRIPTION OF THE DRAWINGS

FIG. 3 is a cross-sectional view through the lead of FIG. 1, taken along the lines 3-3 of FIG. 1.

FIG. 4 is a cross-sectional view through the lead of FIG. 1, taken along the lines 4-4 of FIG. 3.

DETAILED DESCRIPTION

Figure 1:
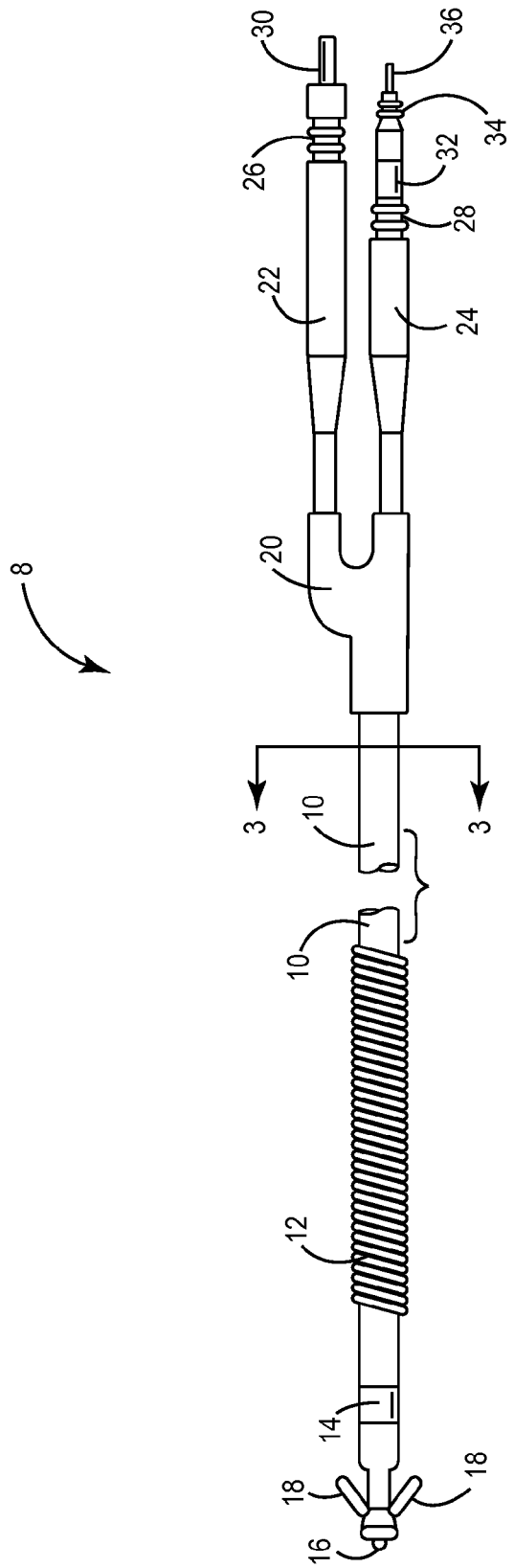
FIG. 1 is a plan view of an implantable lead in accordance with certain embodiments of the invention.

The following discussion is presented to enable a person skilled in the art to make and use the present teachings. Various modifications to the illustrated embodiments will be readily apparent to those skilled in the art, and the generic principles herein may be applied to other embodiments and applications without departing from the present teachings. Thus, the present teachings are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the present teachings. Skilled artisans will recognize the examples provided herein have many useful alternatives and fall within the scope of the present teachings.

FIG. 1 is a plan view of an exemplary defibrillation lead 8 in which the embodiments of the present invention are practiced. However, the embodiments of the present invention may also be usefully practiced in the context of other types of medical electrical leads, such as cardiac pacing leads, nerve and muscle stimulation leads, and so forth. The lead 8 of FIG. 1 is provided with an elongated insulative lead body 10, preferably fabricated of silicone rubber, polyurethane or other biocompatible elastomers. The distal end of the lead 8 carries an elongated defibrillation electrode 12, a ring electrode 14 and a tip electrode 16, each coupled to a conductor located within the lead body 10. Tines 18 may be provided to maintain the electrode 16 in contact with the tissue of the heart, generally the right ventricle. Electrodes 12, 14 and 16 can correspond generally to conventionally available pacing and defibrillation electrodes.

Figure 2:
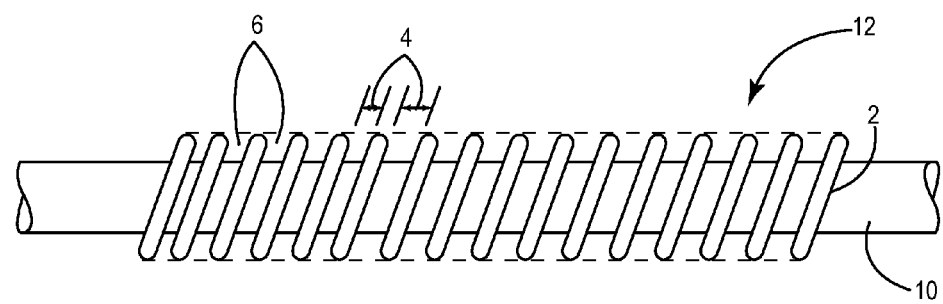
FIG. 2 is an enlarged plan view of a defibrillation electrode of the implantable lead of FIG. 1.

FIG. 2 is an enlarged view of the defibrillation electrode 12. The electrode 12 includes an electrically conductive spring wire 2 formed into a helical coil having proximal and distal ends (not visibly shown). Individual coils of the helical coil are spaced apart to provide gaps 4 between the coils. As will be described (and illustrated) below, the proximal and distal ends of the spring wire 2 extend longitudinally of the helical coil to provide electrical connection points for operatively coupling to one of the conductors within the lead body 10. In certain embodiments, the spring wire 2 of the defibrillation electrode 12 is made of platinum; however, the invention could involve other suitable materials, e.g., tantalum, as well. In certain embodiments, the spring wire 2 has about an 0.005 inch diameter and is wound on an 0.074 inch mandrel at 20 turns per inch to provide a helical coil with a spacing of about 0.017 inch center-to-center between turns, a diameter of about 0.087 inch, and a length of about 3 inches.

The gaps 4 defined by the spring wire 2 are filled with a pliable material 6 which maintains its integrity notwithstanding flexions of the lead body 10 and its conductive coil discharge surface. Such material is often an electrically insulating elastomeric, medical-grade adhesive, e.g., Nusil MED-1137A, so that only the outer peripheral surface of the helical coil spring wire 2 is electrically exposed to the body. However, in embodiments of the invention, the filler material 6 is made to be conductive, thereby providing an increased longitudinal contact body for the defibrillation electrode 12. The filler material 6 extends radially outward from the lead body 10 between the individual coils of the electrode 12.

With reference to FIG. 1, the proximal end of the lead 8 generally carries a connector assembly. In certain embodiments, as shown, the connector assembly begins with a molded lead bifurcation 20, which splits off two of the conductors within lead body 10 to a bipolar, in-line connector assembly 24, generally corresponding to the IS-1 connector standard for pacing leads. However, other types of connector assemblies may also be adapted to practice the present invention. Connector assembly 24 is provided with a first set of sealing rings 28, a connector ring 32, a second sealing ring 34 and connector pin 36. Connector pin 36 is coupled to the conductor which extends through the lead body 10 to the tip electrode 16. The connector ring 32 is coupled to the conductor which extends through the lead body 10 to the ring electrode 14. The conductor coupled to defibrillation electrode 12 extends into connector assembly 22, which carries a set of sealing rings 26 and a connector pin 30, coupled to the conductor extending through lead body 10 to defibrillation electrode 12.

FIG. 3 illustrates a cross-section through the lead body 10, illustrating the inter-relation of conductor lumens 100, 102 and 104 with compression lumens 106, 108 and 110, which are described in more detail in U.S. Pat. No. 5,584,873, issued to Shoberg et al. and incorporated herein by reference in its entirety. In this view, it can be seen that the lumens 100 and 102 contain conductors 112 and 114, which in the illustrated embodiment may take the form of PTFE coated bundled stranded wires having a generally straight configuration. In particular, conductors 112 and 114 may take the form of a PTFE (Polytetrafluoroethylene) coated, bundled, stranded 49 filar cable formed of seven strands, each strand formed of seven filars, as described in more detail in U.S. Pat. No.

5,584,873 by Shoberg et al. incorporated herein by reference in its entirety. Lumen 104 contains a conventional multifilar coiled conductor 116 and a small diameter bundled stranded wire conductor 118. Alternative embodiments, while not shown, may involve the conductor 118 being located within the lumen of conductor 116, rather than external to conductor 116. This embodiment may be particularly advantageous in the context of leads, such as epicardial electrode leads or some nerve and muscle stimulation leads which do not require passage of a stylet through the lumen of coil conductor 116. Conductor 118 may be insulated or uninsulated depending on whether contact between the two conductors along their length is desired.

FIG. 4 is a sectional view through the distal portion of the lead 8, and shows basic mechanisms which may optionally be employed to mechanically interconnect the conductors 112, 114, 116, and 118 at the distal end of the lead 8. These illustrated interconnection mechanisms are intended to be exemplary, and may of course, be employed in conjunction with other components of implantable leads, including other types of electrical connectors to interconnect these conductors with other types of electrodes and to interconnect these components with other lead components such as physiologic sensors such as pressure sensors, oxygen sensors, temperature sensors and the like.

Extending distally from the defibrillation electrode 12, the lead 8 takes the form of a molded piece part carrying the ring electrode 14, which is in turn coupled to stranded conductor 112 (not visible in this view). Electrode 16, as exemplarily illustrated, is a steroid-eluting electrode, provided with a monolithic controlled release device 30 located within a chamber within the electrode. Electrode 16 is coupled to a coiled conductor 116 and 118 by means of an external crimping sleeve 32, which compresses conductor 118 against conductor 116 and compresses conductor 116 against the proximal portion of the electrode 16. Other types of tip electrodes, including screw-in electrodes may of course be substituted for electrode 16. Similarly, other mechanisms may be employed to interconnect conductors 118 and 116 and electrode 16, including welding, swaging, crimping and combinations thereof, including mechanisms disclosed in commonly assigned U.S. Pat. No. 5,676,694 to Boser et al. granted Oct. 14, 1997, and U.S. Pat. No. 6,026,567 granted Feb. 22, 2000, incorporated herein by reference in their entirety.

The conductor 114 passes through an internal lumen 100 within lead body 10, and has its insulation removed in areas in which it passes cross-bore crimp sleeves 36 and 38. The sleeves 36, 38 are preferably fabricated of an inert, conductive metal such as platinum to which the defibrillation electrode 12 can be readily welded. Proximal and distal ends of the defibrillation electrode 12 can be seen respectively at 12A and 12B as occupying the cross bores in the sleeves 36, 38. The sleeves 36, 38 are crimped to the conductor 114 and portions of the proximal end 12A and distal end 12B of the defibrillation electrode 12 are respectively inserted through the cross bores and such entry and exit points of the electrode 12 are respectively laser welded to the corresponding sleeves 36, 38. As previously mentioned with reference to FIG. 1, the conductor 114 serves to couple the defibrillation electrode 12 to an ICD via the connector assembly 22. It should be appreciated that the conductor assembly 22 (including the conductor 114) may be manufactured using any conventional technique known to the art and coupled to the sleeves 36 and/or 38 using any conventional technique known to the art such as crimping, welding, etc.

In certain embodiments, surrounding the proximal portion of defibrillation electrode 12 is an outer insulative sheath 42 which extends proximally to the end of the lead 8. The sheath 42 covers the proximal end 12A of the defibrillation electrode 12. At the distal end of the lead 8, an outer insulative sheath 40 covers the distal end 12B of the defibrillation electrode 12 and may extend distally to one or more pacing electrodes coupled to conductors within the body of the lead 8, as shown. In certain embodiments, the outer insulative sheaths 40, 42 are fabricated of an polyurethane of one of the types typically used in conjunction with cardiac pacing leads and are preferably mechanically coupled to the proximal and distal ends of the defibrillation electrode 12 by means of an adhesive to further stabilize their locations.

It should be appreciated that other lead configurations are just as applicable to the embodiments of the invention, provided that at least one of the electrodes on the lead is a defibrillation electrode (as described herein) or is a further electrode configuration that can be backfilled with a polymeric material. With other lead embodiments, if fewer electrodes are provided on the lead body, correspondingly fewer conductors shall be included in the lead design. However, the incorporation of any defibrillation electrode or other electrode configuration as described above on any lead body can be applicable as described herein.

As mentioned previously, with respect to FIG. 2, the remaining space defined between the individual coils of the defibrillation electrode 12 includes the polymeric material 6. The material 6 is conductive, thereby providing an increased longitudinal contact body for the defibrillation electrode 12. As such, the polymeric material 6 will slightly decrease shocking impedance when compared to equivalent electrodes backfilled with non-conductive polymer. In addition, using the material 6 will attenuate edge effects by reducing current density at metal-insulator edges. In certain embodiments, when molded in place, the polymeric material 6 provides a generally isodiametric and flexible surface for the defibrillation electrodes 12. In certain embodiments, the diameter of the electrodes 12 is one French, or about 0.333 millimeters. The material 6, in certain embodiments, involves an anti-thrombotic/fibrotic compound having releasing agents so as to reduce tissue inflammation. For example, the material 6 can be selected so as to consistently elute nitric oxide.

Generally, the material 6 includes a polymer filled with a conductive filler. In certain embodiments, the polymer is a silicone, for example, a two-part platinum cure adhesive commercially available from NuSil Technology, located in Carpinteria, Calif., U.S.A. It should be appreciated that the polymer could just as well be other suitable materials, such as polyurethane or the like. In certain embodiments, the conductive filler is carbon based fillers, e.g., carbon black. The material 6 can alternatively involve other conductive fillers such as platinum, gold, silver, etc. as well; however, carbon black is embodied herein because it is typically less expensive in comparison to the cost of the others. In certain embodiments, carbon nanotubes (or other like materials), having sizes ranging from nanometer to micrometer and a wide variety of geometries, are used with a polymer as described above, implanted with one or more of the conductive fillers listed above. However, in other embodiments, carbon nanotubes can be used solely with the polymer.

Carbon black filled silicone adhesives can be made to have good conductivity, good polymeric (flexible and strong) mechanical properties, and good adhesion properties to metal. Carbon black is also considered to be at least as inert in comparison to the other alternative fillers referenced above. In contrast to carbon black, some of the alternative fillers are even known to decay especially when using small particles with sizes in the nanometer range. For example, silver particles can corrode in aqueous media in the presence of salts. Alternatively, platinum nanoparticles can be found to sinter when within typical melt-polymer-processing temperature ranges (e.g., about 212° F. to about 572° F., and more typically, about 302° F. to about 437° F.). Therefore, a carbon black filled silicone has good probability to be properly processed and to be biostable and biocompatible. Also, the carbon black filled silicone is solid, which makes it different from other porous conductive materials (e.g. ETFE porous tubing). As such, cell in-growth may be substantially reduced or altogether prevented.

In certain embodiments, the weight ratio of carbon black to silicone is at least 1:10. Using higher ratios of carbon black has been found to promote the conductivity of the composites. However, it has also been determined that using higher ratios of carbon black generally increases the viscosity of the composite before curing and reduces its overall flexibility and/or mechanical properties after curing. Particle size of the carbon black is another important consideration. Generally, smaller particles provide better probability to achieve the balancing, high conductivity, and mechanical properties desired for the composites. It should be realized that optimization can be achieved through adjusting the components in composites and processing methods. In certain embodiments, the percentage by weight of carbon black in the material 6 is at least about 10%. The particle diameter of carbon black is within a range from about 1 to about 100 nanometers. In particular embodiments, the percentage by weight of carbon black in the material 6 is in the range from about 10% to about 20%. In more particular embodiments, the percentage by weight of carbon black in the material 6 is in the range from about 15% to about 18%.

In certain embodiments, the process of providing the material 6 between the coils of the defibrillation electrode 12 involves backfilling of the material 6 with respect to the electrode 12. When using a lead body 10 with multiple lumens (as shown in FIGS. 3 and 4), the process, in certain embodiments, initially involves placing a rigid member (e.g., a stylet) within the lumen 104 of the lead 8 to prevent collapse of the lumen 104 when dispersing the material 6 proximate to the individual coils of the electrode 12. Typically, the size of the rigid member is dictated by the general size of the lumen. In certain embodiments, the rigid member is about 0.016 inch in diameter.

Figure 5:
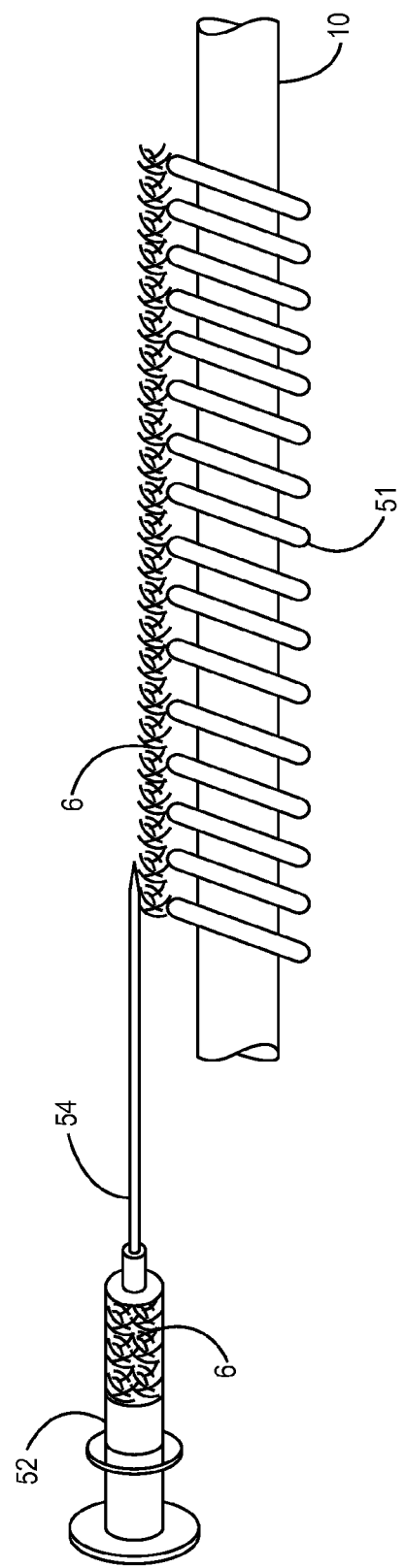
FIG. 5 is a plan view of a helical coil with material being dispensed thereon in accordance with certain embodiments of the invention.

FIG. 5 shows exemplary equipment used in dispensing the material 6. As should be appreciated. many methods can be used in dispensing the material 6 to cover the electrode 12. Typically, a syringe 52 and a corresponding needle 54 are used. In certain embodiments, the syringe 52 is a 1 milliliter syringe. The tip of the syringe 52 is roughened, e.g., using wire cutters, in order to aid its connection to the needle 54. The needle 54 is accordingly secured to the syringe 52. The length of the needle 54 can be modified as desired. Upon filling the syringe 52 with the material 6, the material 6 is subsequently dispensed on an upper surface 56 of the helical coil 51. In certain embodiments, the material 6 is dispensed across an entire upper length of the coil 51 in an even fashion so as to prevent general clumping of the material 6.

Figure 6:
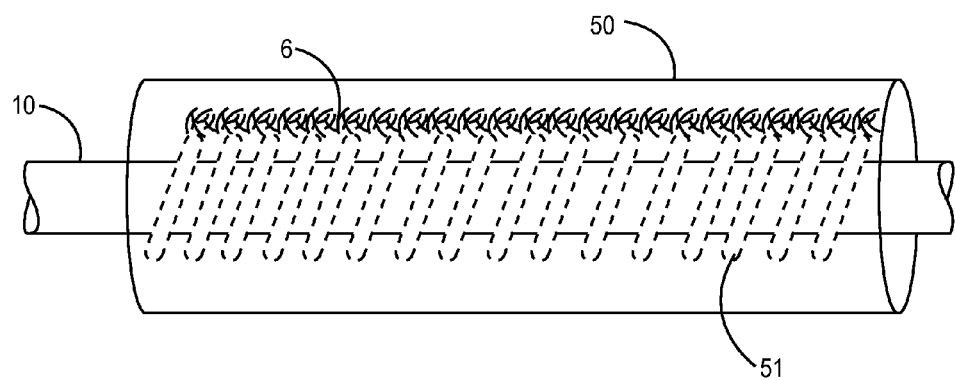
FIG. 6 is a plan view of FIG. 5 with the helical coil inserted in tubing in accordance with certain embodiments of the invention.

As illustrated in FIG. 6, tubing 50, e.g., made of FEP (Fluorinated Ethylene Propylene), having an internal diameter larger than the helical coil 51 of the defibrillation electrode 12, is provided to cover the electrode 12. In certain embodiments, the size ratio of the tubing 50 compared to the helical coil 51 is about 3:1. In more particular embodiments, the ratio is about 2:1, and in even more particular embodiments, the ratio is about 1.6:1. The internal diameter of the tubing 50, in certain embodiments, is about 0.125 inch. The longitudinal ends of the tubing 50 are trimmed to a certain length so that the tubing 50 can cover the helical coil 51. Following the dispensing of the material 6 on the helical coil 51, the tubing 50 is subsequently slid over the coil 51 as shown so as to encase the coil 51 (save for the open ends of the tubing 50).

Figure 7:
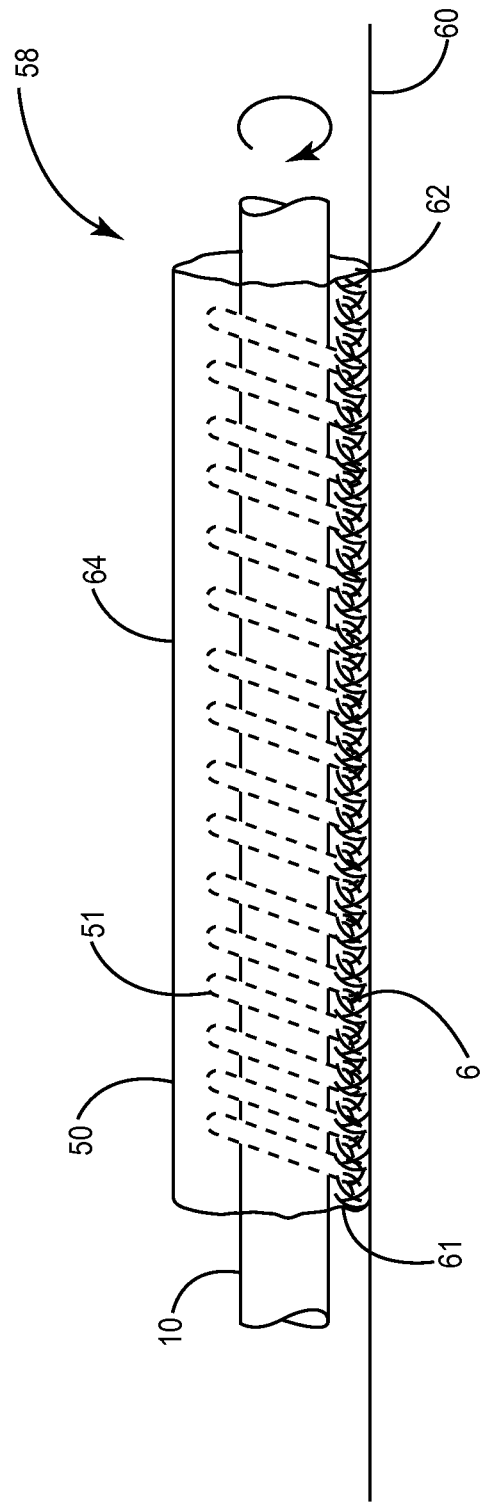
FIG. 7 is a plan view of FIG. 5 with the helical coil being mixed with the material while in the tubing in accordance with certain embodiments of the invention.

As shown in FIG. 7, the assembly 58 including the helical coil 51 and the tubing 50 is then placed on a flat rigid surface 60 with an outer portion 62 of the tubing 50 (e.g., opposite an inner portion 61 of the tubing 50 in proximity to the material 6 on the coil 51) contacting the surface 60. A downward vertical force is then applied on the non-contacting portion 64 of the tubing 50 to ensure that the inner portion 61 of the tubing 50 contacts the helical coil 51 with the bead of material 6. While maintaining the downward vertical force on the tubing 50, the assembly 58 is rolled horizontally across the flat surface 60 to distribute the material 6 evenly across the peripheral surface of the helical coil 51 contained within the tubing 50.

During this rolling procedure, the tubing 50 may stick in one position due to the material 6 clumping on one side of the helical coil 51. As such, in certain embodiments, the assembly 58 may need to be flipped so that the non-contacting portion 64 of the tubing 50 contacts the flat rigid surface 60. Applying a vertical downward force on the opposing side of the tubing 50 while rolling the tubing 50 horizontally should enable the material 6 to be subsequently displaced over any non-covered portions of the helical coil 51.

Figure 8:
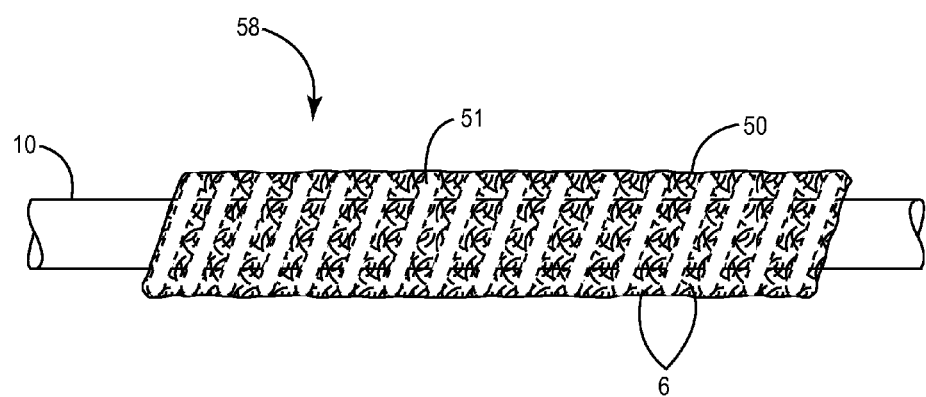
FIG. 8 is a plan view of FIG. 7 following shrinking of the tubing in accordance with certain embodiments of the invention.

Once the material 6 is evenly distributed over the helical coil 51, the assembly 58 is cured. As should be appreciated, the curing of the assembly 58 can be accomplished using any of a number of known methods. One of these methods includes heat curing. When the silicone adhesives are heat cured, in certain embodiments, the assembly 58 is cured using a heat gun. The heat gun is directed at the assembly 58, with the heat gradually applied along the length of the assembly 58 while the assembly 58 is rotated. In certain embodiments, the heat gun is set at a temperature of about 550° F. and is directed at the assembly for a duration of five minutes. While the heat gun is set at a temperature of about 550° F., the heat gun is generally used with a nozzle extension. As such, the temperature achieved outside of the nozzle extension is typically about 375° F., generally found to be a suitable temperature for shrinking the tubing 50 of the assembly 58. It should be appreciated that both the temperature and time parameters can be adjusted accordingly without departing from the spirit of the invention. For example, if the heat gun is set at a temperature lower than 550° F., then the curing period can, in turn, be conducted for a duration greater than five minutes. As shown in FIG. 8, following this curing or heating operation, the tubing 50 shall have decreased in size or shrunk so that its inner diameter generally comes in contact with the outer diameter of the helical coil 51. As a result, the material 6 is distributed evenly between the individual coils of the helical coil 51. In certain embodiments, the outer peripheries of the material 6 shall be distributed about the helical coil 51 so as to generally form an isodiametric assembly.

Figure 9:
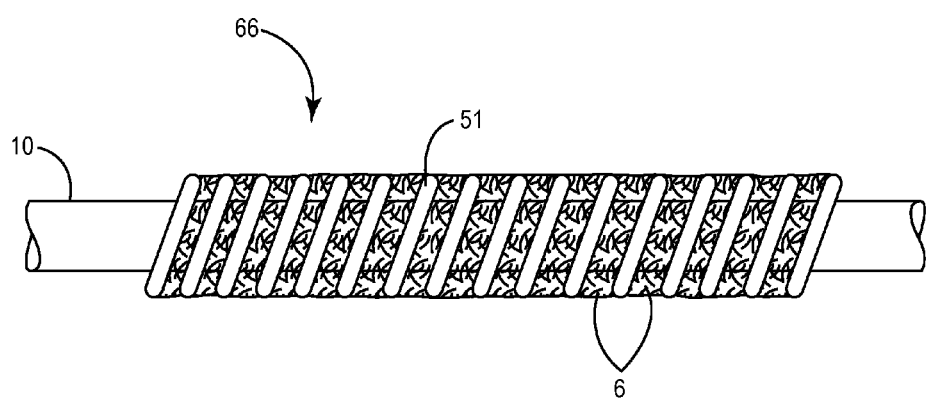
FIG. 9 is a plan view of FIG. 7 following removal of the tubing in accordance with certain embodiments of the invention.

Subsequently, the assembly 58 can be allowed to cool; however, in certain embodiments, this cooling step can be eliminated altogether. The tubing 50 is removed so that a structure 66 defined by the helical coil 51 and the material 6 is exposed. In certain embodiments, the tubing 50 can be removed using a razor blade. As illustrated in FIG. 9, once the tubing 50 is removed, one can see that the structure 66 is generally isodiametric, wherein the diameters of the material 6 and the helical coil 51 (measured by the outer peripheries of each of the material 6 and the helical coil 51) differ by thousandths of an inch. In certain embodiments, the diameters of the material 6 and the helical coil 51 differ by no more than two thousandths of an inch (0.002 inches).

In certain embodiments, the backfilling process is modified so as to create a defibrillation electrode having an overmolded or overcoated electrode surface. As such, the defibrillation electrode is produced so as to have the material 6 entirely cover the helical coil 51. This structure can be provided by modifying the process described above. In certain embodiments, a greater amount of material 6 is dispensed within the assembly 58 per the syringe 52 and the heating procedure is modified so that the tubing 50 shrinks to a resulting inner diameter that is larger than that previously described herein (the tubing 50 is not shrunk enough to generally create contact between the tubing 50 and the outer periphery of the helical coil 51). One consequence of using an overmolded electrode surface is that the geometric surface area of the resulting electrode is reduced; however, a smooth atraumatic electrode surface is created. As such, the electrode surface can greatly reduce fibrotic encapsulation and improve extractability of the lead. One particular application for this design is the creation of an ultra-long defibrillation electrode from the RV apex to the mid RA chamber (generally about 10-14 cm long), creating a very large shadow area or electric field to reduce defibrillation energy. Previous lead designs have not traversed the tricuspid valve with a defibrillation electrode for fear of possibly damaging the valve leaflet and function.

Figure 10:
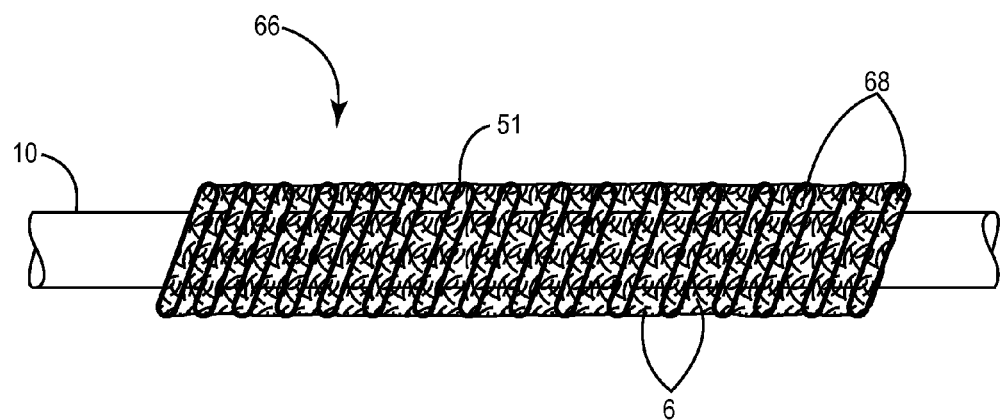
FIG. 10 is a plan view of a defibrillation electrode in accordance with certain embodiments of the invention.

In certain embodiments, the backfilling process is modified to incorporate carbon nanotubes onto the helical coil 51. The carbon nanotubes will further aid in masking the exposed outer periphery of the helical coil 51. As such, addition of the carbon nanotubes will further prevent fibrous ingrowth on the exposed portions of the helical coil 51 and aid in the extractability of the lead 8, while still being able to provide a delivery of a defibrillation shock through the carbon nanotubes. In certain embodiments, the helical coil 51 is dipped in carbon nanotube powder 68 prior to the tubing 50 being placed over the helical coil 51. As shown in FIG. 10, following the process steps involving dispensing the material 6, evenly distributing the material 6 within the assembly 58, curing the assembly 58, and removing the tubing 50 from the assembly 58, the carbon nanotube powder 68 shall remain on the exposed surface area of the helical coil 51 of the defibrillation electrode.

In certain embodiments, the material 6 can alternatively be moisture cured. As such, once dispersed on the helical coil 51, the material 6 can be cured with controlled moisture levels at room temperature. As is known, using such a curing procedure, the molding process needs to be designed with particularity to ensure enough moisture is diffused into the composite levels. Such curing techniques will generally not require use of the tubing 50; however, other known methods of distributing the material 6 evenly with respect to the individual coils of the helical coil 51 would need to be initially utilized prior to curing the material 6. Other curing processes are also possible depending on the curing process needed by the polymer components.

It will be appreciated the embodiments of the invention can take many forms. The true essence and spirit of the embodiments of the invention are defined in the appended claims, and it is not intended the embodiment of the invention presented herein should limit the scope thereof.

What is claimed is:

1. A method of fabricating a medical electrical electrode comprising:
   sliding an elongated conductive coil over a length of a lead body;
   dispensing an electrically conductive polymer material on the elongated conductive coil, wherein dispensing the electrically conductive polymer material further includes injecting the electrically conductive polymer material from a syringe;
   disposing a tubing over the elongated conductive coil;
   distributing the electrically conductive polymer material between individual turns of the elongated conductive coil such that the electrically conductive polymer material is in electrical contact with the elongated conductive coil;
   heating the tubing so the tubing shrinks around the elongated conductive coil; and
   removing the tubing.

2. The method of claim 1, wherein the tubing is sized to encase the elongated conductive coil.

3. The method of claim 1 wherein the tubing comprises fluorinated ethylene propylene.

4. The method of claim 1 wherein the size ratio of the tubing to the elongated conductive coil is no greater than about 3:1.

5. A method of fabricating a medical electrical electrode comprising:
   sliding an elongated conductive coil over a length of a lead body;
   dispensing an electrically conductive polymer material on the elongated conductive coil;
   disposing a tubing over the elongated conductive coil;
   distributing the electrically conductive polymer material between individual turns of the elongated conductive coil such that the electrically conductive polymer material is in electrical contact with the elongated conductive coil, wherein distributing the electrically conductive polymer material further includes rolling the tubing over a flat surface such that the electrically conductive polymer material flows between the individual turns of the elongated conductive coil;
   heating the tubing so the tubing shrinks around the elongated conductive coil; and
   removing the tubing.

6. The method of claim 5, wherein heating the tubing further includes heating the tubing to a temperature of about 375° F. and heating the tubing for about five minutes.

7. The method of claim 5, wherein heating the tubing further includes shrinking the tubing so the tubing contacts individual coils of the elongated conductive coil.

\* \* \* \* \*